United States Patent [19]

Earnshaw et al.

[11] Patent Number: 5,196,307
[45] Date of Patent: Mar. 23, 1993

[54] CLONED HUMAN CENTROMERE AUTOANTIGEN

[75] Inventors: William Earnshaw, Monkton, Md.; Don Cleveland, Baltimore, both of Md.; Kevin F. Sullivan, San Diego, Calif.

[73] Assignee: The Johns Hopkins University, Baltimore, Md.

[21] Appl. No.: 174,854

[22] Filed: Mar. 29, 1988

[51] Int. Cl.$^5$ .................. C12N 15/12; G01N 33/531; G01N 33/564
[52] U.S. Cl. ............................. 435/7.9; 435/172.3; 435/243; 435/252.3; 435/320.1; 436/508; 436/518; 436/536; 436/543; 536/23.5; 935/12
[58] Field of Search ................. 435/7, 70, 172.3, 320, 435/235, 69.3, 71.2, 243, 252.3, 252.8, 7.95, 320.1, 7.9; 436/508, 525, 543, 518, 536; 536/27; 935/12, 24, 27

[56] References Cited

U.S. PATENT DOCUMENTS 4,751,181  6/1988  Keene .................................. 436/506

OTHER PUBLICATIONS

Sullivan and Glass, 1991, Chromosoma 100:360–370.
E. A. Kabat, Structural Concepts in Immunology and Immunochemistry, Holt, Rinehart and Winston, Inc., New York, 1968, pp. 82–91.
Tijssen, Practice and Theory of Enzyme Immunoassays, Elsevier, Amsterdam, 1985, pp. 333–334.
Earnshaw et al. Clinical Research, 33, 591A, 1985.
Moroi, et al., "Autoantibody to Centromere (kinetochore) in scleroderma sera", Proc. Natl. Acad. Sci. USA, (1980) 77, 1627–1631.
Cox, et al., "Human Anticentromere Antibodies: Distribution, Characterization of Antigens, and Effect on Microtubule Organization, Cell", (1983), 35, 331–339.
Nishikai, et al., Characterisation of centromere (kinetochore) antigen reactive with sera of patients with a scleroderma variant (CREST Syndrome), Annals of the Rheumatic Diseases, (1984) 43, 819–824.
Guldner, et al., "Human anti-centromere sera recognise a 19.5 kD non-histone chromosomal protein from HeLa cells", Clin. Exp. Immunol., (1984) 58, 13–20.
Palmer, et al., "Kinetochore Components Recognized by Human Autoantibodies are Present on Mononucleosomes, Molecular and Cellular Biology", (1985) 5, 173–186.
Beutner, et al., "Evaluation of Methods for Detection of Anticentromere Antibodies and Other Antinuclear Antibodies", J. Am. Acad. Dermat., (1985) 12, 289–295.
Valdivia, et al, "Fractionation and Initial Characterization of the Kinetochore from Mammalian Metaphase Chromosomes", J. Cell Biol., (1985), 101, 1124–1134.
Earnshaw, et al, "Identification of a Family of Human Centromere Proteins Using Autoimmune Sera from Patients with Scleroderma", Chromosoma (1985), 19, 313–321.

(List continued on next page.)

Primary Examiner—David Saunders
Attorney, Agent, or Firm—Banner, Birch, McKie & Beckett

[57] ABSTRACT

The invention relates to DNA molecules coding for human CENP-B polypeptides. The invention provides DNA molecules comprising an epitopically functional part of the cDNA sequence of human CENP-B polypeptide. The invention also provides cloning vehicles capable of replication and expression comprising cDNA molecules coding for human CENP-B polypeptide. The invention further provides for hosts transformed with a vehicle having a cDNA molecule coding for human CENP-B polypeptide. In another embodiment, the invention provides for the detection of autoantibodies to human CENP-B using the human CENP-B polypeptide encoded for by the cDNA molecules of the invention. Also, the invention provides monoclonal antibodies, and hybridomas which produce them, which bind an epitope on human CENP-B which corresponds to an epitope to which autoantibodies to human CENP-B bind.

10 Claims, 7 Drawing Sheets

OTHER PUBLICATIONS

Earnshaw, et al, "Three related Centromere Proteins are Absent from the Inactive Centromere of a Stable Isodicentric Chromosome", Chromosoma, (1985), 92, 290–296.

Valdivia, et al., in Vallee, ed., "Structural and Contractile Proteins", Methods in Enzymol., (1986) 134, 268–280.

Ringertz, et al., "Computer Analysis of the Distribution of Nuclear Antigens: Studies on the Spatial and Functional Organization of the Interphase Nucleus", J. Cell Sci. Suppl., (1986), 4, 11–28.

Earnshaw et al., "Three Human Chromosomal Autoantigens are Recognized by Sera from Patients with Anti-Centromere Antibodies", J. Clin. Invest., (1986), 77, 426–430.

Palmer et al., "A 17-kD Centromere Protein (CENP-A) Copurifies with Nucleosome Core Particles and with Histones", J. Cell Biol., (1987) 104, 805–815.

Kingwell, et al., "Mammalian kinetochore/centromere composition: a 50 kDa Antigen is present in the Mammalian kinetochore/centromere", Chromosoma, (1987), 95, 403–407.

Del Mazo, et al., "Centromeric Proteins Recognized by CREST Sera and Meiotic Chromosome Segregation", Chromosoma (1987), 96, 55–59.

Earnshaw, et al., "Molecular Cloning of cDNA for CENP-B, the Major Human Centromere Autoantigen", J. Cell Biol., (1987) 104, 817–829.

Earnshaw, et al., "Analysis of Anticentromere Autoantibodies Using Cloned Autoantigen CENP-B", Proc. Natl. Acad. Sci. USA, (1987) 84, 4979–4983.

FIG. IA

```
                                        10
                        CGA CAG CTG ACG TTC CGG GAG AAG TCA
                        arg gln leu thr phe arg glu lys ser
                                        40
ATC GCG CGG CGC TTC AAC ATC CCG CCG TCC ACG CTG AGC ACG
ile ala arg arg phe asn ile pro pro ser thr leu ser thr
                                        70
GTG GCC TCC ACC TGC CGC AAG ACC AAC AAG CTG TCT CCC TAC
val ala ser thr cys arg lys thr asn lys leu ser pro tyr
                                        100
GCC GGC CTG CCG GTC AAG GGC ATC ATC CTC AAG GAG AAG GCG
ala gly leu pro val lys gly ile ile leu lys glu lys ala
                                        130
GGC TGG CTG GAC CGC TTC CGC GGC CGC CAC GGC GTG GTG TCC
gly trp leu asp arg phe arg arg arg his gly val val ser
                                        160
CCG GCG GCG CCT GCC AGT CCG GCC GCG GTG CCC TCG GAG GGC
pro ala ala pro ala ser pro ala ala val pro ser glu gly
                                        190
TCG GTG GCC GAG GGC TAC GCC TCG CAG GAC GTG TTC AGC GCC
ser val ala glu gly tyr ala ser gln asp val phe ser ala
                                        220
CTG TGC GGA GGC GAC GGA CGG CCG CGT CAA GCC ACC CAG CGC
leu cys gly gly asp gly arg pro arg gln ala thr gln arg
                                        250
CCG CTG GTG GCC GGC AAG TCG GCC AAG CCC CGC GCA GGC CAA
pro leu val ala gly lys ser ala lys pro arg ala gly gln
                                        280
ACC CAG GCC CTG GCC AAG TAC TTG AAG GCC TTG GAC ACC CGA
thr gln ala leu ala lys tyr leu lys ala leu asp thr arg
                                        310
GCC CAG TCC TTG GAC ACC TCG GGC CTG CGG CAT GTG CAG CTG
ala gln ser leu asp thr ser gly leu arg his val gln leu
```

FIG. 1B

```
              [CNPB3:20                                                    30
         CGG ATC ATC CAG GAG GTG GAG GAG AAT CCG GAC CTG CGC AAG GGC GAG
         arg ile ile gln glu val glu glu asn pro asp leu arg lys gly glu 50                                           60
         ATC CTG AAG AAC AAG CGC GCC ATC CTG GCG TCG GAG CGC AAG TAC GGG
         ile leu lys asn lys arg ala ile leu ala ser glu arg lys tyr gly 80                                           90
         GAC AAG CTC GAG GGC TTG CTC ATC GCC TGG TTC CAG CAG ATC CGC GCC
         asp lys leu glu gly leu leu ile ala trp phe gln gln ile arg ala 110                                          120
         CTG CGC ATA GCC GAG GAG CTG GGC ATG GAC GAC TTC ACC GCC TCC AAC
         leu arg ile ala glu glu leu gly met asp asp phe thr ala ser asn 140                                          150
         TGC AGC GGC GTG GCC CGC GCC CGC GCG CGA AAC GCT GCC CCC CGC ACC
         cys ser gly val ala arg ala arg ala arg asn ala ala pro arg thr

[CNPB2:        170                                          180
         AGT GGC GGG AGC ACT ACT GGT TGG CGC GCT CGG GAG GAG CAG CCG CCG
         ser gly gly ser thr thr gly trp arg ala arg glu glu gln pro pro 200                                          210
         ACC GAG ACC AGT CTA TGG TAC GAC TTC CTG CCC GAC CAG GCC GCG GGG
         thr glu thr ser leu trp tyr asp phe leu pro asp gln ala ala gly 230                                          240
         CTG AGC GTC CTG CTA TGC GCC AAT GCC GAC GGC AGC GAG AAG CTG CCC
         leu ser val leu leu cys ala asn ala asp gly ser glu lys leu pro 260                                          270
         GCC GGC CTG CCC TGC GAC TAC ACC GCC AAC TCC AAG GGT GGT GTC ACC
         ala gly leu pro cys asp tyr thr ala asn ser lys gly gly val thr 290                                          300
         ATG GCT GCA GAG TCT CGC CGG GTC CTG CTG TTG GCC GGC CGC TTG GCT
         met ala ala glu ser arg arg val leu leu leu ala gly arg leu ala 320                                          330
         GCC TTC TTC CCT CCC GGC ACC GTG CAT CCG CTG GAG AGG GGA GTG GTC
         ala phe phe pro pro gly thr val his pro leu glu arg gly val val
```

FIG. IC

```
                                        340
CAG CAG GTG AAG GGC CAC TAC CGC CAG GCC ATG CTG CTC AAG
gln gln val lys gly his tyr arg gln ala met leu leu lys 370
CTC ACG GAG GCC CTG CAC TTT GTG GCT GCC GCC TGG CAG GCA
leu thr glu ala leu his phe val ala ala ala trp gln ala 400
GGT GGC CCT AAT GCC ACC ATC ACC ACT TCC CTC AAG AGT GAG
gly gly pro asn ala thr ile thr thr ser leu lys ser glu 430
GAA GGA GAG GAA GAG GAG GAG GAA GGG GAG GAG GAG GAG GAG
glu gly glu glu glu glu glu glu gly glu glu glu glu glu CNPB1 :                                 460
GAG GGT GAT GTT GAT AGT GAT GAA GAA GAG GAG GAA GAT GAG
glu gly asp val asp ser asp glu glu glu glu glu asp glu 490
GTG GAG GCC GGT GGC AGC TTC GGG GCT TAT GGT GCC CAG GAG
val glu ala gly gly ser phe gly ala tyr gly ala gln glu 520
GAT TCA GAC AGT GAG GAA GAG GAC GAT GAG GAA GAG GAT GAT
asp ser asp ser glu glu glu asp asp glu glu glu asp asp 550
GTA CCC AGC TTT GGG GAG GCC ATG GCT TAC TTT GCC ATG GTC
val pro ser phe gly glu ala met ala tyr phe ala met val 580
ATC CTC CAC TTG GAA CAC GAT CTG GTT CAT GTG ACC ATG AAG
ile leu his leu glu his asp leu val his val thr met lys
```

GTCACTGGACCTAGCTGTGCCCCCAACCTAGATTGGCAGCACCACCCCAGGGCAGA
CTTCCCCTGGTCCTGCAACAGGCCCGGTCACCTCGGCCGGGCCCGGGGCTGAGGTC
GCTCAGGGGACCAGGTGGGGCGGGTGGGGAGCTGTCCGGTGCTACCACACCGTGCC
CTCTCCCCTCTGCCATCCACGTCAGGTCTTTGGTGGGGGGACCCCAAAGCCATTCT
ACCCCCCAGGCCGCCTGAGAAGCACAGTTAACTCACTGCGGGCTCCTGAGCCTGCT
GTTTTCTTTCCAGATTGGAGGTTTCCAAGAGGCCCCCCACCGTGGAAGTAACCAAG
CCTGGGCAGAGGGGCCTGGGGCTGGGCCCAGAGTCCAGCCGTCCAGNTGCTCCTTT
AAAAAAAAAAAAAAAAAAAAAAAAA

FIG. 1D

```
                    350                                                 360
GCC ATG GCC GCG CTA GAG GGC CAG GAT CCC TCA GGC CTG CAG CTG GGT
ala met ala ala leu glu gly gln asp pro ser gly leu gln leu gly 380                                                 390
GTG GAG CCT TCG GAC ATA GCC GCC TGC TTT CGT GAG GCT GGC TTT GGG
val glu pro ser asp ile ala ala cys phe arg glu ala gly phe gly 410                                            420
GGA GAG GAA GAG GAG GAG GAG GAG GAA GAA GAG GAG GAG GAA GAG GGT
gly glu glu glu glu glu glu glu glu glu glu glu glu glu glu gly 440                                            450
GAA GGG GGG GAA GGA GAG GAA TTG GGG GAG GAA GAG GAG GTG GAG GAG
glu gly gly glu gly glu glu leu gly glu glu glu glu val glu glu 470                                            480
GAG AGC TCC TCG GAG GGC TTG GAG GCT GAG GAC TGG GCC CAG GGA GTA
glu ser ser ser glu gly leu glu ala glu asp trp ala gln gly val 500                                                 510
GAA GCC CAG TGC CCT ACT CTG CAT TTC CTG GAA GGT GGG GAG GAC TCT
glu ala gln cys pro thr leu his phe leu glu gly gly glu asp ser

530                                                 540
GAA GAT GAA GAC GAC GAT GAT GAT GAG GAG GAT GGT GAT GAG GTG CCT
glu asp glu asp asp asp asp asp glu glu asp gly asp glu val pro 560                                                 570
AAG AGG TAC CTG ACC TCC TTC CCC ATT GAT GAC CGC GTG CAG AGC CAC
lys arg tyr leu thr ser phe pro ile asp asp arg val gln ser his 590                                       599
AAC CAC GCC AGG CAG GCG GGA CTT CTA GGT CTT GGA CAT CAA AGC TGA
asn his ala arg gln ala gly leu leu gly leu gly his gln ser  *

GGACTCTCTGGGCACCCGCTGTGCATGGAGCCAGAGTGCAGAGCCCCAGATCCTTTAGTAATG
AGCCTCACTGCCGTGCTTATTGCCTCTTTCTCAGAATCCTCTTTCCTCCCCATTTGGCCCTGG
CTCAGTGGACTAACCACAGCAGCAGCCAGGGATGGGCCCTGGAGGTTCCCGGCCGGAGAGTGC
GGGAAGGGCTCCAGAAGAAGGTCCAGCCTAGGCCCCCTGCAAGGCTGGCAGCCCCCACCCCCC
    TCTGCCTGCTTTCCACCTCCCCAGTCCCTTTCTCTGGCCCTGTCCATGTGACTTTGGCCCTTG
    GGCGCTTCCTTGTGGGCAGCTGCAGGCCCCATGCCTCTCCTCCCTCTCTCTGGCAGGGCCCAT
         CCCAGTTTGATTTCAATAAATCTGTCCACTCCCCTTTTGTGGGGGTGAACGTTTTAACAGCCA
```

CLONED HUMAN CENTROMERE AUTOANTIGEN

BACKGROUND OF THE INVENTION

This work was supported a Grant from the National Institutes of Health. The U.S. Government may retain certain rights in this invention.

FIELD OF THE INVENTION

The present invention relates to the use of recombinant DNA technology for the transformation of a host with eukaryotic genetic sequences for the expression of centromere polypeptides and methods of using recombinantly produced centromere polypeptides to detect anticentromere antibodies.

DESCRIPTION OF THE BACKGROUND ART

The centromere is that region of a eukaryotic chromosome which is attached to the spindle during nuclear division. Aside from its normal role in cell division, the centromere is also of interest since in certain autoimmune diseases anticentromere autoantibodies (ACA) are produced. This is especially true for rheumatic diseases. ACA were discovered in 1980, when it was found that certain patients with the calcinosis/Raynauds phenomenon/esophegeal dysmotility/scleroactyly/elangiectasiae (CREST) variant of scleroderma produce autoantibodies that recognize the centromere region of chromosomes. Though ACA are closely associated with the CREST syndrome, the only clinical finding common to all ACA+ individuals is Raynauds phenomenon.

Rheumatic diseases are characterized by the production of autoantibodies directed against nuclear and cytoplasmic autoantigens. The reasons for autoantibody expression are generally unknown and many theories seeking to explain the phenomenon are currently under consideration. In particular, it is not known if the autoimmune response results from a classical antigen-driven immunization or is a result of aberrations in the mechanisms that normally control the immune system. Although much progress has been made in identifying and characterizing autoantigens, the origin of antinuclear autoantibodies remains obscure. It has been suggested that autoantibodies might arise as a result of fortuitous cross-reactions exhibited by normal antibodies, as a result of chance mutations causing normal B-cell clones elicited by foreign antigen to change specificity and recognize self components, or as antiidiotypes elicited during an immune response against a viral protein. These models could explain an autoimmune response against any single epitope, but they cannot account for the ACA response, since multiple structurally independent epitopes requiring multiple chance events are targeted in virtually every affected individual.

Prior immunoblotting analysis has revealed that approximately 96% of a test group of 39 ACA+ sera recognized three chromosomal polypeptides of 17 kDA (CENP-A), 80 kDa (CENP-B), and 140 kDa (CENP-C) (Earnshaw, et al.,*Journal of Clinical Investigation*, 77: 426, 1986). Affinity purified antibodies to CENP-B cross-reacted with CENPs A and C, indicating that these antigens are structurally related (Earnshaw, et al., *Chromosoma*, 91: 313, 1985). Antibodies to CENP-B are present at high titer in all ACA+ sera examined, whereas the titer of autoantibodies to CENPs A and C is occasionally lower.

Since the various types of autoimmune disease can be characterized based upon the specificity of autoantibodies which are produced, the ability to detect autoantibodies reactive with the centromere polypeptides would be of great value in the characterization of autoimmune disease. Unfortunately, the existing commercial systems detect anticentromere autoantibodies by utilizing dividing cells which contain nuclear autoantigens other than the centromere. These systems will detect antibodies which react with nuclear polypeptides other than the centromere and, as a result, may give false positive results which can lead to an incorrect classification. In addition, these existing systems are awkward to perform and difficult to scale up to enable testing of large numbers of samples. Thus, there is considerable need for a system which efficiently detects only antibodies to the centromere and not other nuclear polypeptides.

Presently, chromosomes are sorted by reacting them with dyes which bind to DNA. The presence of these dyes is then detected by irradiating the chromosomes. Unfortunately, this irradiation can damage or break the DNA of the chromosomes thereby complicating the sorting process. Consequently, there is a need for a way to sort or classify chromosomes with minimal damage to the chromosome.

SUMMARY OF THE INVENTION

It is a major object of the present invention to provide a DNA sequence which encodes essentially the entire human CENP-B polypeptide.

Another object of the present invention is to provide a host cell transformed or transfected with a DNA sequence which encodes human CENP-B polypeptide such that the host cell can express this polypeptide.

Yet another object of the present invention is to provide a biologically functional plasmid or viral DNA vector which includes a DNA sequence encoding human CENP-B polypeptide.

It is still another object of the present invention to provide a DNA sequence comprising a DNA sequence encoding a polypeptide which has an amino acid sequence possessing at least one epitope for autoantibodies to human CENP-B.

It is an object of the invention to provide a method of producing human CENP-B polypeptide in host cells.

Another object of the present invention is to provide a method of detecting autoantibodies to human CENP-B polypeptide.

It is a further object of the present invention to provide a monoclonal antibody that binds an epitope on human CENP-B, wherein the monoclonal antibody epitope corresponds to an epitope which binds autoantibodies to human CENP-B. The invention further includes hybrid cell lines which produce these monoclonal antibodies.

These and other objects are provided by one or more of the following embodiments of the present invention. In one embodiment a DNA sequence is provided which encodes essentially the entire human CENP-B polypeptide.

In another embodiment a biologically functional plasmid or viral DNA vector is provided which includes a DNA sequence encoding for human CENP-B polypeptide.

In another embodiment, a method of producing human CENP-B polypeptide is presented which comprises providing a host cell which can replicate and express an intron-free DNA sequence of human CENP-B polypeptide, growing the host cell, and recovering the human CENP-B polypeptide. Also contemplated by the present invention are the transformed or transfected host cells themselves.

In yet another embodiment human CENP-B polypeptide is provided which is substantially free of other nuclear polypeptides.

In still another embodiment, a method of detecting autoantibodies to human CENP-B polypeptide is provided which comprises contacting a sample with the polypeptide expressed by the DNA sequence of the invention, incubating the sample with the polypeptide for a period of time and under conditions sufficient for the autoantibodies to bind to the polypeptide, separating the autoantibodies which are bound to the polypeptide from the rest of the sample, and detecting the presence of the autoantibodies which are bound to the polypeptide or eluted therefrom.

A major advantage of the present invention is that it provides the art with a ready source of human CENP-B polypeptide which is similar to that purified from natural sources, while avoiding the problems associated with the isolation of naturally occurring human CENP-B polypeptide to separate it from other eukaryotic non-CENP-B polypeptides. This absence of non-CENP-B eukaryotic polypeptides is significant in that it allows the development of test systems which will only detect autoantibodies specifically reactive with human CENP-B polypeptide.

Another advantage of providing human CENP-B polypeptide in host cells is that by so doing it is possible to obtain much larger quantities of the polypeptide than are currently practicably available from natural sources. As a consequence, not only is it possible to use the polypeptide of the invention to more accurately classify patients with such autoimmune rheumatic diseases as CREST, but it is now possible to also provide commercially useful quantities of human CENP-B polypeptide for use in diagnostic systems.

A further advantage of the invention is that the novel monoclonal antibodies provided herein bind an epitope on CENP-B and, in so doing, can prevent the binding of autoantibodies to the corresponding autoimmune epitope. Thus, these monoclonal antibodies are useful in sensitive immunoassays, such as competitive immunoassays to measure the presence of autoantibodies to this epitope.

Another advantage of the monoclonal antibodies of the invention is that they can be used to distinguish among and sort the various chromosomes of the nucleus. Due to differences in the amount of CENP-B polypeptide present in various chromosomes, different chromosomes will bond different amounts of the monoclonal antibodies of the invention.

Still another advantage of these monoclonal antibodies is that they can be used to affinity purify CENP-B polypeptide from natural sources or from the surrounding polypeptide milieu, such as when the CENP-B polypeptide is cloned in eukaryotes.

DESCRIPTION OF THE DRAWINGS

FIGS. 1A-1D present the DNA and predicted protein coding sequence for CENP-B. The sequence of 2,625 bases of the CENP-B mRNA was determined by the dideoxy DNA method. The sequence was obtained from the overlapping cDNA clones CENP-B1 (also known as $C_{term}$ CENP-B), CENP-B2, CENP-B3, CENP-B4 and $N_{prox}$ CENP-B a subclone of CENP-B4 corresponding to the 5' 1041 bases of CENP-B4. In all cases, sequences of each cDNA clone were indentical in regions of overlap. The sequence was unambiguously determined on both DNA strands. Shown below the DNA sequence is the predicted polypeptide sequence, representing the majority of the protein sequence for CENP-B. Boxed areas indicate regions of CENP-B which are comprised predominantly of acidic residues.

FIG. 2 shows the distribution of epitopes recognized by ACA. Cloned antigens: All are present only on CENP-B and are localized to the hybrid proteins as shown. The precise location of the epitope within a given shaded segment is not known. aa, Amino acids. Chromosomal antigens: These determinants have been defined (Earnshaw, et al., *Chromosoma*, 91: 313, 1985). None of them is present on cloned CENP-B, although epitopes 4 and 5 are present on chromosomal CENP-B (Earnshaw, et al., ibid).

FIG. 3 shows the use of $C_{term}$ CENP-B[beta-gal] in a RIA to detect ACA. The RIA shows binding of various patient and control sera to $C_{term}$ CENP-B[beta-gal]. Each dot is the average of three measurements for the serum from a different individual. (Inset) Isolation of partly purified $C_{term}$ CENP-B[beta-gal] from induced lysogens. Lane 1, marker proteins (molecular masses indicating in kDa to the left of the gel). Lanes 2-4, Coomassie blue staining of proteins of whole cell lysate (lane 2), soluble protein fraction (lane 3), and final fraction (lane 4). Lanes 5-7, immunoblotting analysis of the samples of lanes 2-4 using patient serum GS (1:1000).

FIG. 4 demonstrates that binding in the RIA is specific for cloned human CENP-B. FIG. 4B: Comparison of the RIA of FIG. 4 and the described immunoblotting results. The relevant portions of the immunoblots were excised and counted in a gamma counter. The two sets of results were normalized to give an equivalent average value.

DETAILED DESCRIPTION

The present invention relates to the manipulation of genetic materials by recombinant procedures which make possible the production of polypeptides possessing part or all of the primary structural conformation for at least one epitope for binding autoantibodies to human CENP-B. These polypeptides are highly useful for the immunological detection of autoantibodies reactive with them since such autoantibodies are indicative of autoimmune rheumatic diseases.

The present invention describes the isolation of a series of overlapping CENP-B cDNA clones, and subclones derived from them, used to characterize this 80-kD human centromere autoantigen recognized by patients with anticentromere autoantibodies. The cloned sequences encode a polypeptide with an apparent molecular mass appropriate for native CENP-B, as developed more fully in Example 1 below. The cloned polypeptide and native CENP-B share three non-overlapping epitopes. The first two are defined by murine monoclonal antibodies elicited by injection of cloned fusion protein. Epitope 1 reacts with m-ACA1 (HB 9667) and corresponds to a major antigenic site recognized by the autoantibody to CENP-B used to obtain the original clone. This epitope is present on the $C_{term}$ CENP-B polypeptide of the invention and is destroyed by disruption at a site 42 amino acids from the carboxyl terminus. While epitope 2 is recognized by murine monoclonal antibody m-ACA2, it is not recognized by most autoantibodies. These epitopes have been shown to be distinct both by competitive binding experiments and by their presence or absence on different subcloned portions of the fusion protein.

The third independent epitope, recognized by a subset of anti-centromere-positive patient sera, is present on the $N_{prox}$ CENP-B polypeptide of the invention and maps to a region substantially close to the amino terminus of the CENP-B fusion polypeptide.

DNA and RNA blot analyses indicate that CENP-B is unrelated to CENP-C, a 140-kD centromere antigen that is also recognized by these autoimmune antisera. CENP-B is the product of a 2.9-kb mRNA that is encoded by a single genetic locus. This mRNA is far too short to encode a polypeptide the size of CENP-C. The carboxyl terminus of CENP-B contains two long domains comprised almost entirely of glutamic and aspartic acid residues. These domains may be responsible for anomalous migration of CENP-B on SDS-polyacrylamide gels, since the true molecular mass of CENP-B is approximately 65 kD, 15 kD less than the apparent molecular mass deduced from gel electrophoresis. Quite unexpectedly, immunofluorescence analysis using antibodies specific for CENP-B reveals that the levels of this antigen vary widely between chromosomes.

The development of specific DNA sequences for splicing into DNA vectors can be accomplished using a variety of techniques. For example, alternative methods which can be employed include: (1) the isolation of a double-stranded DNA sequence from the genomic DNA of the eukaryote; (2) the chemical manufacture of a DNA sequence to provide the necessary codons for the polypeptide of interest; and (3) the in vitro synthesis of a double-stranded DNA sequence by reverse transcription of mRNA isolated from a eukaryotic donor cell. In the latter case, a DNA complement of mRNA is formed which is generally referred to as cDNA.

The manufacture of DNA sequences is frequently the method of choice when the entire sequence of amino acid residues of the desired polypeptide product is known. When the entire sequence of amino acid residues of the desired polypeptide is not known, the direct manufacture of DNA sequences is not possible and the method of choice is the formation of cDNA sequences. Among the standard procedures for isolating cDNA sequences of interest is the formation of plasmid-carrying cDNA libraries which are derived from reverse transcription of mRNA which is abundant in donor cells which have a high level of genetic expression. In those cases where significant portions of the polypeptide's amino acid sequence are known, the production of labeled single stranded DNA probe sequences duplicating a sequence putatively present in the target cDNA may be employed in DNA/DNA hybridization procedures which are carried out on cloned copies of the cDNA which have been denatured into a single stranded form (Jaye, et al., *Nucleic Acid Research*, 11:2325, 1983).

Hybridization procedures are useful for the screening of recombinant clones by using labeled mixed synthetic oligonucleotide probes wherein each is potentially the complete complement of a specific DNA sequence in the hybridization sample which includes a heterogeneous mixture of single stranded DNAs or RNAs. These procedures are particularly useful in the detection of cDNA clones derived from sources where extremely low amounts of mRNA sequences relating to the polypeptide of interest are present. In other words, by using stringent hybridization conditions directed toward avoidance of nonspecific binding it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

Of the three above-noted methods for developing specific DNA sequences for use in recombinant procedures the use of genomic DNA isolates is the least common. This is especially true when it is desirable to obtain the microbial expression of mammalian polypeptides.

In another aspect, the present invention provides novel polypeptides of human CENP-B which have part or all of the primary structural conformation, that is, a continuous sequence of amino acid residues possessing at least one epitope for autoantibodies to human CENP-B.

The term "polypeptide," as applied to the human CENP-B polypeptide of the invention, denotes a sequence of amino acids having an epitope for autoantibodies to human CENP-B, wherein the sequence of amino acids is encoded by all or part of the cDNA sequence of the invention.

The polypeptides resulting from microbial expression of the DNA sequences of the invention can be further characterized by their freedom from association with other human polypeptides or other contaminants which might otherwise be associated with human CENP-B in its natural cellular environment or in such extracellular fluids as plasma or urine.

The term "host" includes not only prokaryotes, but also such eukaryotes as yeast, filamentous fungi, as well as plant and animal cells which can replicate and express an intron-free DNA sequence of human CENP-B. However, prokaryotes are preferred as the host organism.

The term "prokaryotes" is meant to include all bacteria which can be transformed or transfected with the eukaryotic gene for the expression of human CENP-B polypeptide. Prokaryotic hosts may include gram negative as well as gram positive bacteria such as, for example, *E. coli, S. typhimurium, Serratia marcescens* and *Bacillus subtilis.*

A recombinant DNA molecule coding for the human CENP-B polypeptide can be used to transform or transfect the host using any of the techniques commonly known to those of ordinary skill in the art. Especially preferred is the use of a plasmid or a virus containing the human CENP-B polypeptide coding sequence for purposes of prokaryotic transformation or transfection, respectively.

Methods for preparing fused, operably linked genes and expressing them in hosts are well-known in the art (Maniatis, et al., *Molecular Cloning: A Laboratory Manual*, Cold Spring Harbor Laboratory, Cold Spring Harbor, N.Y., 1981). The genetic constructs and methods described therein can be utilized for expression of human CENP-B polypeptide.

In general, expression vectors containing promoter sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The polypeptides of the invention can then be isolated from the growth medium, cellular lysates, or cellular membrane fractions.

The isolation and purification of the microbially expressed polypeptides of the invention may be by any conventional means such as, for example, preparative chromatographic separations and immunological separations such as those involving the use of monoclonal or polyclonal antibody. The monoclonal antibody of the invention, which is produced by HB 9667, is especially useful in affinity purification of human CENP popypeptides.

By having provided the sequence of amino acid residues of human CENP-B polypeptide, the present invention provides for the manufacture of DNA sequences which code for the host expression of polypeptide analogs or derivatives of human CENP-B polypeptide which differ from naturally-occurring forms in terms of the identity or location of one or more amino acid residues and which share some or all of the properties of naturally-occurring polypeptide forms.

The novel DNA sequences of the invention include all sequences useful in providing the expression in host cells of polypeptides which have at least a part of the primary structural conformation and at least one the epitopes of human CENP-B polypeptide which are comprehended by: (a) the DNA sequence as set forth in FIG. 1 or its complementary strand; (b) DNA sequences which hybridize to DNA sequences defined in (a) or fragments thereof; and (c) DNA sequences which, but for the degeneracy of the genetic code, would hybridize to DNA sequences defined in (a) and (b) above. Specifically comprehended in (b) are genomic DNA sequences which encode allelic variant forms of human CENP-B polypeptide. Part (c) specifically comprehends the manufacture of DNA sequences which encode human CENP-B polypeptide, human CENP-B polypeptide fragments and human CENP-B polypeptide analogs wherein the DNA sequences thereof may incorporate codons which facilitate translation of mRNA in nonvertebrate hosts.

Since the cDNA sequence of the invention encodes essentially the entire human CENP-B molecule it is now a matter or routine to prepare, subclone and express smaller polypeptide fragments of cDNA from this or a corresponding cDNA sequence which would encode as few as one epitope for autoantibodies to human CENP-B. The presence of such an epitope on a cloned polypeptide can then be determined using, for example as described herein, sera from a patient with autoantibodies to CENP-B.

The human CENP-B polypeptide of the invention is particularly suited for use in immunoassays in which it can be utilized in liquid phase or bound to a solid phase carrier. In addition, the human CENP-B polypeptide used in these assays can be detectably labeled in various ways.

Examples of immunoassays which can utilize human CENP-B polypeptide of the invention are competitive and non-competitive immunoassays in either a direct or indirect format. Examples of such immunoassays are the radioimmunoassay (RIA), the sandwich (immunometric) assay and the Western blot assay. Detection of autoantibodies which bind to the human CENP-B polypeptide of the invention can be done utilizing immunoassays which run in either the forward, reverse, or simultaneous modes, including immunohistochemical assays on physiological samples. Regardless of the type of immunoassay which is used, the concentration of human CENP-B polypeptide utilized can be readily determined by one of ordinary skill in the art.

The human CENP-B polypeptide of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses and magnetite. The nature of the carrier can be either soluble in insoluble for purposes of the invention. Those skilled in the art will know of other suitable carriers for binding human CENP-B polypeptide, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, the autoantibody which binds to the human CENP-B polypeptide of the invention may be present in various biological fluids and tissues. Any sample containing a detectable amount of autoantibodies to human CENP-B polypeptide can be used. Normally, a sample is a liquid such as urine, saliva, cerebrospinal fluid, blood, serum and the like, or a solid or semi-solid such as tissue, feces and the like.

The present invention also relates to monoclonal antibodies which recognize an epitope on human CENP-B which corresponds to the epitope recognized by autoantibodies to human CENP-B. These monoclonal antibodies are highly useful for immunological detection of CENP-B and in connection with the diagnosis of autoimmune disease.

The general method used for production of hybridomas secreting monoclonal antibodies is well known to those of ordinary skill in the art. Illustrative of the techniques utilized in the present invention are those described in *Proceedings of the National Academy of Science, USA*, 75: 3405, (1978).

In brief, female BALB/c mice were immunized over a 30 day period with human CENP-B polypeptide. Ten days after the final immunization, the animals were sacrificed and spleen cells fused with a mouse nonsecretor myeloma cell line. Hybridomas were screened for antibody production and positive clones were tested for monoclonal antibody binding to human CENP-B polypeptide.

The isolation of other hybridomas secreting monoclonal antibodies with the specificity of the monoclonal antibodies of the invention can be accomplished by one of ordinary skill in the art, for example, by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with the same idiotype as the antibody of the hybridoma used for immunization.

Idiotypic identity between monoclonal antibodies of two hybridomas suggests that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

When comparing two epitopes, the term "corresponds to" means that the two epitopes are the same or so closely related that the binding of monoclonal antibody inhibits the binding of autoantibody.

Alternatively, it is possible to evaluate, without undue experimentation, a monoclonal antibody to determine whether it has the same specificity as the monoclonal antibody of the invention by determining whether the monoclonal antibody being tested prevents the monoclonal antibody of the invention from binding to human CENP-B polypeptide, with which the monoclonal antibody of the invention is normally reactive. If the monoclonal antibody being tested competes with the monoclonal antibody of the invention, as shown by a decrease in binding by the monoclonal antibody of the invention, then it is considered that the two monoclonal antibodies bind to the same epitope.

Under certain circumstances, monoclonal antibodies of one isotype might be more preferable than those of another in terms of their diagnostic efficacy. Particular isotypes of a monoclonal antibody can be prepared either directly, by selecting from the initial fusion, or prepared secondarily, from a parental hybridoma secreting monoclonal antibody of different isotype by using the sib selection technique to isolate class-switch variants (Steplewski, et al., *Proceedings of National Academy of Science, USA*, 82: 8653, 1985; Spira, et al., *Journal of Immunological Methods*, 74: 307, 1984). Thus, the monoclonal antibodies of the invention would include class-switch variants having the specificity of monoclonal antibody m-ACA1 which is produced by ATCC HB 9667.

The term "antibody" as used in this invention is meant to include intact molecules as well as fragments thereof, such as, for example, Fab and F(ab')$_2$, which are capable of binding the epitopic determinant.

The monoclonal antibodies of the invention are particularly suited for use in immunoassays, especially competitive immunoassays, in which they can compete with autoantibodies for binding to their corresponding epitopes.

Another use for the monoclonal antibodies of the invention is to distinguish among the various chromosomes of the nucleus. Since the monoclonal antibodies bind specifically to an epitope found on CENP-B polypeptide and since the amount of CENP-B polypeptide varies among chromosomes, different chromosomes will bind different amounts of monoclonal antibody. Since the presence of the monoclonal antibody, in turn, can be detected using techniques known in the art, such as, for example, a fluorescent label, it is possible to sort chromosomes based on differences in the amount of detectably labeled antibody which is present on a given chromosome. This approach to sorting chromosomes, unlike existing techniques which utilize DNA dyes and irradiation, has minimal disruptive effect on the DNA of the chromosome. Thus, the determination of nucleotide sequences of the various chromosomes can be much more expeditiously accomplished using the monoclonal antibodies of the invention.

Still another use for the monoclonal antibodies of the invention is in the affinity purification of CENP-B polypeptides. For example, the monoclonal antibodies of the invention can be bound to a solid phase support and then used to purify native or cloned CENP-B polypeptide which is essentially free of other polypeptides. Thus, by using this approach CENP-B polypeptide cloned in eukaryotic hosts can be purified such that it is essentially free of other potential non-CENP-B polypeptides. Those skilled in the art will know of other protocols for affinity purification using the monoclonal antibodies of the invention.

Monoclonal antibody m-ACA1 can be utilized in the present invention. Monoclonal antibody m-ACA1 is obtained from, or has the identifying characteristics of, an antibody obtained from the cell line 2D-7 having ATCC accession number HB 9667. This cell line was placed on deposit for 30 years at the American Type Culture Collection (ATCC) in Rockville, Md. prior to Mar. 29, 1988.

The above disclosure generally describes the present invention. A more complete understanding can be obtained by reference to the following specific examples which are provided herein for purposes of illustration only and are not intended to limit the scope of the invention.

EXAMPLE 1

Cloning and Expression of CENP-B Peptides

A. Isolation of cDNA Clones

An initial cDNA clone was isolated using the lambda-gt11 expression method of Young and Davis (*Proceedings of the National Academy of Sciences, USA*, 80:1194, 1983) from a cDNA library constructed from human endothelial cell mRNA. (This library was provided by M. Chow, D. Littman, and R. Axel.) Approximately $9 \times 10^5$ recombinant phage were plated on lawns of *Escherichia coli* RY1090, production of fusion protein induced by overlaying nitrocellulose filters (BA83, Schleicher & Schuell, Inc., Keene, N.H.) impregnated with isopropylthiogalactoside (Sigma Chemical Co., St. Louis, Mont.), and immunopositive colonies detected by processing the filter as though for immunoblotting (see below).

Filters were screened with serum GS at a dilution of 1:1,000. Preadsorption of this serum with bacterial lysates was found to be unnecessary. By this method, one clone was detected and eventually plaque purified. This clone, lambda-CENP-B1, contained a cDNA insert of 1,282 bp.

Phage clones containing longer cDNA inserts were obtained by screening a cDNA library constructed from human placental mRNA (Clonetech) by DNA plaque hybridization. Further screening of $2.7 \times 10^5$ phage from the original library yielded no phage with cDNA inserts longer than lambda-CENP-B1. In all cases the plaque lifts were processed by standard procedures (Maniatis, et al., in *Molecular Cloning, A Laboratory Manual*, Cold Spring Harbor Press, Cold Spring Harbor, N.Y., 1981). Probes were labeled with alpha $-^{32}$P-dATP or alpha $-^{32}$P-dCTP using random priming with either reverse transcriptase (Life Science Associates, Bayport, N.Y.) (Shank, et al., *Cell*, 15:1383, 1978) or DNA polymerase I, Klenow fragment (New England Biolabs, Beverly, Mass.) (Feinberg, et al., *Annals of Biochemistry*, 132:6, 1983).

B. Expression of CENP-B as Fusion Protein in Bacteria

For expression of cDNA from CENP-B1-4 as fusion proteins with the bacterial protein trpE, appropriate regions of cDNA were cloned into one of the pATH series of bacterial expression plasmids (Koerner, T. J., Duke University). This series of plasmids was specifically engineered to contain a polylinker of unique restriction endonuclease sites within the carboxy-terminal coding sequences of the trpE protein. Because the polylinker is inserted in each of the three different reading frames in the various pATH plasmids, any exogenous cDNA fragment can conveniently be cloned such that its encoded polypeptide is in frame with the trpE protein in one of the plasmids as long as compatible restriction sites are available.

For expression of CENP-B1 (also known as $C_{term}$ CENP-B), CENP-B2, CENP-B3, CENP-B4 and subclone $N_{prox}$ CENP-B derived from CENP-B4, each cDNA was excised with Eco RI from the original lamda clone, or from pUC9 subclones and the fragment isolated after electrophoresis on low melting temperature agarose gels. The gel slices were melted and added the appropriate pATH plasmid that had been linearized with Eco RI and treated with alkaline phosphatase. The mixtures were then diluted into DNA ligase buffer (New England Biolabs), brought to room temperature, and DNA ligase added for 2 h to overnight. Ligation reactions were transformed by standard methods into *Escherichia coli* strains DH1 (Hanahan, *Journal of Molecular Biology*, 166:557, 1983) of CAG-456 which is a temperature-sensitive strain of *E. coli* that contains a mutation which prevents expression of a number of stress induced proteases. Transformants were selected by ampicillin resistance and plasmids carrying the recombinant trpE-CENP-B fusion gene were identified by colony hybridization. Restriction mapping of isolated plasmid DNA identified those plasmids into which the cDNA had been cloned in the proper orientation.

TrpE-CENP-B fusion proteins were induced from overnight cultures of CAG-456 transformants harboring the desired plasmids that were grown at 30° C. in M9 (Maniatis, et al., ibid) supplemented with 100 ug/ml ampicillin, and 20 ug/ml tryptophane. The overnight culture was diluted 1:10 into the same medium without tryptophane. The bacteria were incubated at 30° C. for 2 h and the tryptophane operon induced for an additional 2 h by addition of indoleacrylic acid (Sigma Chemical Co.) to 5 ug/ml. Bacteria were lysed by boiling in SDS gel sample buffer and proteins resolved by PAGE (Laemili; *Nature*, 227, 680, 1970).

For expression of amino- and carboxyl-terminal sequences of CENP-B1, a subclone of CENP-B1 in pBR322 was linearized at the unique Asp 718 site within the coding portions of the cDNA. The 5' overhang produced was filled in by Klenow DNA polymerase and 1 uM dTTP, dGTP, dCTP, and dATP. A portion of the reaction was digested with Eco RI and the 318-base fragment corresponding to the more NH$_2$-terminal sequences of CENP-B1 was cloned into pATH 11 that had been digested with Eco RI and Sma I. For expression of the carboxy-terminal sequences of CENP-B1, the remaining aliquot was digested with Hind III at the pBR322 Hind III site, 29 bp 3' to the terminus of CENP-B1 sequences. The appropriate fragment was then purified by gel electrophoresis, and cloned into pATH 3 digested at the Bam HI site in the polylinker which was filled in with Klenow and then digested with Hind III.

For expression of the amino-terminal portion of CENP-B4 ($N_{prox}$ CENP-B), CENP-B4 cDNA was double digested with Bam HI and Eco RI and the 1,050-base fragment corresponding to the 5' portion of CENP-B4 was cloned into Eco RI-Bam HI-digested pATH 11.

For expression of CENP-B2 as a fusion protein with a smaller bacterial moiety consisting of 16 amino-terminal residues: four from beta-galactosidase and 12 from polylinker sequences, the entire CENP-B2 cDNA was subcloned into the Eco RI site of pUC9. This construction placed CENP-B2 expression in frame and under control of the lac operon. Fusion protein was induced in a fashion analogous to that for trpE proteins with the exception that the inducer was 10 uM isopropylthiogalactoside.

EXAMPLE 2

Immunological Techniques

A. Affinity Purification

Antibodies were affinity purified from antigens immobilized on nitrocellulose blots by exposure to 3M NH$_4$-K-thiocyanate (Earnshaw, et al., *Chromosoma*. 91:313, 1985).

B. Immunoblotting

Antigen on nitrocellulose strips was preincubated with PTX-BSA (10 mM NaPO$_4$, pH 7.5, 0.2% Triton X-100, 0.15M NaCl, 1 mM EGTA, 1 mM NaN$_3$ containing 4% BSA; Miles Pentex) for 20 min. Antibody was added to this and incubated for the desired time. Nonbound antibody was removed by washing five times for 3 min with GB (50 mM triethanolamine-HCl, pH 7.5; 0.5% Triton X-100, 0.1M NaCl, 2 mM K-EDTA, 0.1% SDS), the strips were then rinsed briefly with one change of PTX, and incubated with PTX-BSA for 5 min. $^{125}$I-Protein A (or rabbit anti-mouse IgG for the mAbs) was then added ($1 \times 10^6$ cpm/ml PTX-BSA) for 1 h, after which the strips were again washed five times for 3 min each with GB. Subsequently, the strips were dried, mounted on cardboard, and bound probe detected by autoradiography.

C. Indirect immunofluorescence

Indirect immunofluorescence was performed using colcemid-arrested HeLa cells spread by centrifugation on glow-discharged coverslips (Earnshaw, et al., *Chromosoma*, 92:290, 1985). Briefly, bound antibody was detected with biotinylated second antibody (anti-human, anti-rabbit, or anti-mouse; Vector Laboratories, Inc., Burlingame, Calif.) and streptavidin linked to Texas Red (Bethesda Research Laboratories, Bethesda, Md.). Slides were examined with an Olympus BH-2 microscope and images were obtained on Kodak Tri-X film, ASA-1000.

EXAMPLE 3

Preparation of Polyclonal Anticentromere Antibodies

Fusion protein, $C_{term}$ CENP-B[beta-gal], also known as CENP-B1, was isolated from RY1089 lysogens harboring phage lambda-CENP-B1 by a simple differential sedimentation procedure. Briefly, frozen induced lysogens were disrupted with lysozyme, EDTA, sonication, and detergent, releasing a granule of fusion protein. This granule was separated from soluble and membrane proteins by three cycles of sedimentation at 10,000 g (15 min) in the presence of 1% Triton X-100 in TEN buffer (10 mM Tris, pH 7.4, 1 mM Na EDTA, 50 mM NaCl). The granule was then dissolved in 8M urea in TEN buffer at 65° C., insoluble material removed by centrifugation at 12,500 g for 10 min, and then dialyzed overnight versus TEN buffer.

Two male rabbits (6 mo; Harlan Sprague Dawley, Inc., Indianapolis, Ind.) were injected at days 0, 29, 80, 122, and 152 with 70 ug of solubilized $C_{term}$ CENP-B[beta-gal]. The first injection used Freund's complete adjuvant; subsequent injections used Freund's incomplete adjuvant. Injections were given at multiple sites: subcutaneous, intramuscular, and intraperitoneal. Animals were bled from the ear on days 0, 38, 92, 135, and 169 by venipuncture. One rabbit responded by producing antibodies that recognize CENP-B in immunoblots of isolated chromosomes. This polyclonal anticentromere antiserum was designed ra-ACA1.

EXAMPLE 4

Preparation of Monoclonal Anticentromere Antibodies

Eight BALB/c mice were injected intraperitoneally with 200 ug of crude $C_{term}$ CENP-B[beta-gal] on days 0 and 30. The mice were bled on day 40 and tested for production of antibodies binding to CENP-B. Two mice responded and were given subsequent booster injections on days 52, 53, 54, and 55. On day 55, spleens from these two mice were removed; spleenocytes were mixed together and subsequently fused to the P3-X63-Ag8.653 nonsecreting myeloma cell line (Kearney, et al., *Journal of Immunology*, 123:1548, 1979; Kiehart, *Journal of Cell Biology*, 99:1002, 1984). The fusion mixture was plated in four 96-well plates (Nunc, Roskilde, Denmark). As colonies appeared, culture supernatants were screened by ELISA against $C_{term}$ CENP-B[beta-gal] and beta-galactosidase (Sigma Chemical Co.). Wells positive for the former and negative for the latter were designated possible anti-human candidates and were cloned in soft agar (Kiehart, et al., ibid). Wells positive on both ELISAs were assumed to be producing anti-beta-galactosidase, and several of these cloned as well.

Primary clones were screened by immunoblotting against $C_{term}$ CENP-B[trpE]. Positive wells immediately recloned in soft agar. All clones that showed binding to $C_{term}$ CENP-B[trpE] also bound to chromosomal CENP-B. Four independent clones (m-ACA1, m-ACA2, m-ACA3, and m-ACA4) were obtained. Competitive binding experiments (Kiehart, et al., ibid) showed that m-ACA1 and m-ACA4 bind to overlapping determinants on $C_{term}$ CENP-B[trip-E]. The same is true of m-ACA2 and m-ACA3.

EXAMPLE 5

Characterization of Cloned CENP-B

A. Isolation CENP-B cDNA

To identify cDNA clones for human centromere autoantigens, a lambda-gt11 expression library was screened (Young, et al., ibid) using serum from a patient with anticentromere antibodies (ACAs).

Selection of the antiserum was critical. Many antisera from these patients have high titers of ACAs, but most also have other autoantibodies that recognize a variety of cellular components. Serum GS (from a patient with Raynaud's phenomenon and scleroderma) was chosen as the most suitable of the 38 ACA(+) antisera available. This serum contains 375 ug/ml (or 3% of the total) of IgG specific for the 80-kD centromere autoantigen CENP-B and is negative for other common autoantibodies, including Ro, La, Sm, DNA (ss and ds), RNP, Scl-70 (topoisomerase I), actin, and intermediate filaments. Serum GS binds detectibly to CENP-B in immunoblots of isolated chromosomal proteins at dilutions of up to 1:600,000.

When serum GS was used to screen a lambda-gt11 library constructed from human endothelial cell mRNA, immunopositive plaques were detected at a frequency of about 1/50,000. After plaque purification, Eco RI digestion of purified phage DNA from an initial isolate, lambda-CENP-B1, liberated a single cDNA fragment of 1,282 bp.

Using nucleic acid hybridization with this insert, no longer cDNA inserts in the original library were found, but a second lambda-gt11 cDNA library from human placenta yielded three longer clones (lambda-CENP-B2 [2,133 bp], lambda-CENP-B3 [2,578 bp], and lambda-CENP-B4 [2,625 bp]).

Immunological Analysis of the Polypeptide Encoded by lambda-CENP-B1

When bacteria lysogenic for lambda-CENP-B1 were induced to express the lac operon they produced a 150-kD polypeptide consisting of the cloned protein fused to beta-galactosidase. Autoantibodies from GS antiserum purified by binding to this fusion protein (immobilized on nitrocellulose) bound to centromeres and to CENP-B on blots of human chromosomal proteins, but not to CENP-A or CENP-C.

To verify that the protein encoded by lambda-CENP-B1 is authentic CENP-B, rabbit polyclonal antibodies and murine monoclonal antibodies were prepared to the $C_{term}$ CENP-B protein fused to beta-galactosidase ($C_{term}$ CENP-B[beta-gal]). The isolated protein used for immunization was approximately 40% pure.

One rabbit produced antibodies (designated ra-ACA1) that not only recognized centromeres by indirect immunofluorescence, but also bound to CENP-B on immunoblots of total chromosomal proteins. Preimmune sera did not bind in these assays nor did the immune serum bind to CENPs A or C.

Mice were immunized with $C_{term}$ CENP-B[beta-gal] and hybridomas were screened with a $C_{term}$ CENP-B[trp E] fusion protein to obtain two cloned cell lines secreting monoclonal antibodies to $C_{term}$ CENP-B (m-ACA1 and m-ACA2). The use of the trpE fusion protein enabled the elimination of hybridomas recognizing beta-galactosidase. m-ACA1 and m-ACA2 were shown to bind to centromeres and CENP-B on blots of chromosomal proteins. When tested for binding to trpE fusion proteins containing 104 residues from the NH$_2$ terminus or 43 residues from the COOH terminus of C$_{term}$ CENP-B, m-ACA2 bound to the NH$_2$-terminal region but neither autoimmune serum GS nor m-ACA1 bound to either subfragment of C$_{term}$ CENP-B. Therefore, m-ACA 1 and 2 bind to distinct epitopes on C$_{term}$ CENP-B[trpE], a conclusion that is further supported by the observation that m-ACA 2, but not m-ACA 1, binds to a proteolytic fragment derived from the fusion protein. The data also shows that the autoepitope spans the junction between the two subcloned portions of C$_{term}$ CENP-B or, less likely, that the epitope may be located close to this site and may not adopt a native conformation in the trpE fusion protein.

Overall, these data demonstrate that m-ACA 1 and 2 bind to distinct sites on C$_{term}$ CENP-B[trpE]. Since both antibodies also bind to CENP-B, the cloned fusion protein and CENP-B contain at least two epitopes in common.

Thus, five independent lines of evidence show that the cloned cDNA encodes authentic CENP-B. First, expression of the cDNA in a bacterial vector yielded an immunoreactive fusion polypeptide that bound (and can be used to affinity purify) antibodies against CENP-B. Second, the apparent size of SDS PAGE and acidic pI of the nearly full-length cloned protein are appropriate for CENP-B. Third, polyclonal antibodies raised against the cloned fusion protein also recognize chromosomal CENP-B. Fourth, two mAbs that recognize distinct, non-overlapping epitopes on the cloned fusion protein also recognize the corresponding epitopes on chromosomal CENP-B. Fifth, autoimmune sera recognize at least two distinct sites present both on authentic CENP-B and on the polypeptide encoded by the cloned CENP-B4 cDNA.

CENP-B is encoded by a single human chromosomal locus that is transcribed into a single 2,900-base mRNA of which about 90-95% has been cloned herein. The predicted partial polypeptide sequence of 594 amino acids is most remarkable for the presence of two very highly acidic domains, together comprising almost 100 residues that are more than 80% glutamic or aspartic acid. The only significant homologies detected in the Los Alamos or Dayhoff sequence banks were to other proteins with extensive acidic regions.

Although the polyacidic regions are the most striking features of the primary sequence, the data of Table I indicates that the carboxy terminus of this polypeptide is unusual as well, since the carboxy-terminal 151-amino acid residues impart a 16-21-kD shift in apparent mobility in SDS PAGE relative to the true molecular mass. For example, it was determined that monoclonal antibody m-ACA recognizes two polypeptides in bacterial extracts producing C$_{term}$ CENP-B[trpE]. The smaller polypeptide is apparently a proteolytic fragment derived from the larger one. These polypeptides migrate as though they contain 20 and 38 Kd, respectively, of human polypeptide attached to 32 kD of bacterial trpE protein. However, the total human insert present in this clone encodes only 18 kD of human polypeptide. The reason for this abnormal migration in SDS PAGE is unknown.

TABLE I

| Anomalous Migration of Fusion Proteins Containing CENP-B | | | | |
|---|---|---|---|---|
| Fusion protein | Vector | True molecular mass (kD) | Apparent molecular mass (kD) | Discrepancy |
| C$_{term}$ CENP-B-[beta-gal] | lambda-gt11 | 133 | 150 | 17 |
| C$_{term}$ CENP-B-[trpE] | pATH 11 | 50 | 68 | 18 |
| fp-trpE-CENP-B2 | pATH 3 | 79 | 102 | 23 |
| fp-Bgal-CENP-B2 | pUC9 | 48.5 | 71 | 22.5 |
| CENP-B4[trpE] | pATH 11 | 97 | 123 | 26 |

EXAMPLE 6

Analysis of Anticentromere Antibodies Using Cloned Autoantigen CENP-B

A. Cloned Peptides

C$_{term}$CENP-B[beta-gal] consists of the amino-terminal 113-kDa portion of beta-galactosidase linked to the carboxyl terminal 147 amino acids of CENP-B. As described above, the monoclonal antibodies m-ACA1 and m-ACA2, recognize two nonoverlapping determinants on CENP-B.

C$_{term}$CENP-B [trpE] consists of the 147 carboxyl-terminal amino acid residues of cloned CENP-B fused to the bacterial TrpE protein. C$_{term}$CENP-B$_L$ and C$_{term}$-CENP-B$_R$ were produced by further subdividing the human portion of C$_{term}$CENP-B into segments of 104 amino-terminal and 43 carboxyl-terminal amino acid residues, respectively, and expressing these as TrpE fusion proteins.

Figure 1A:
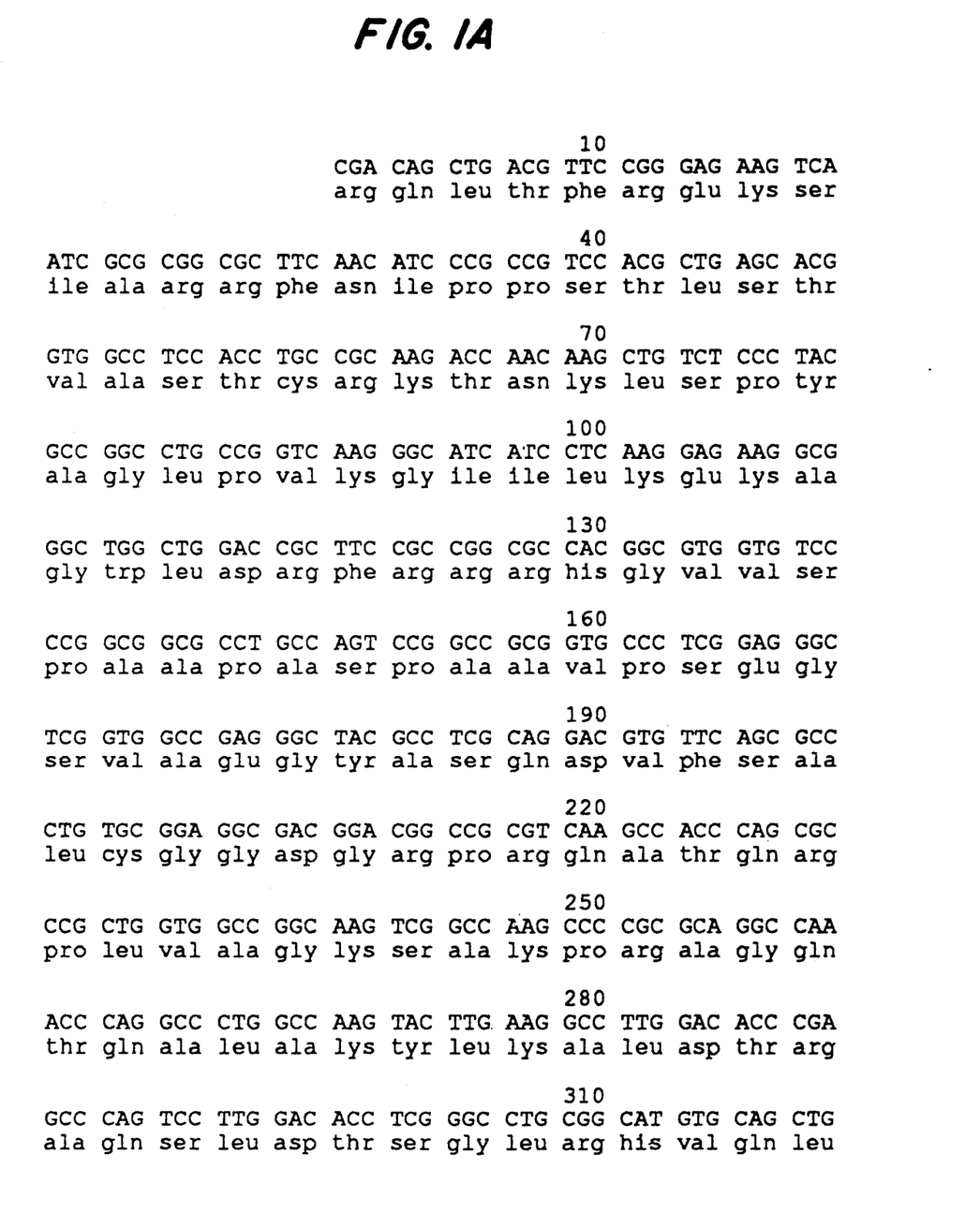
Figure 1B:
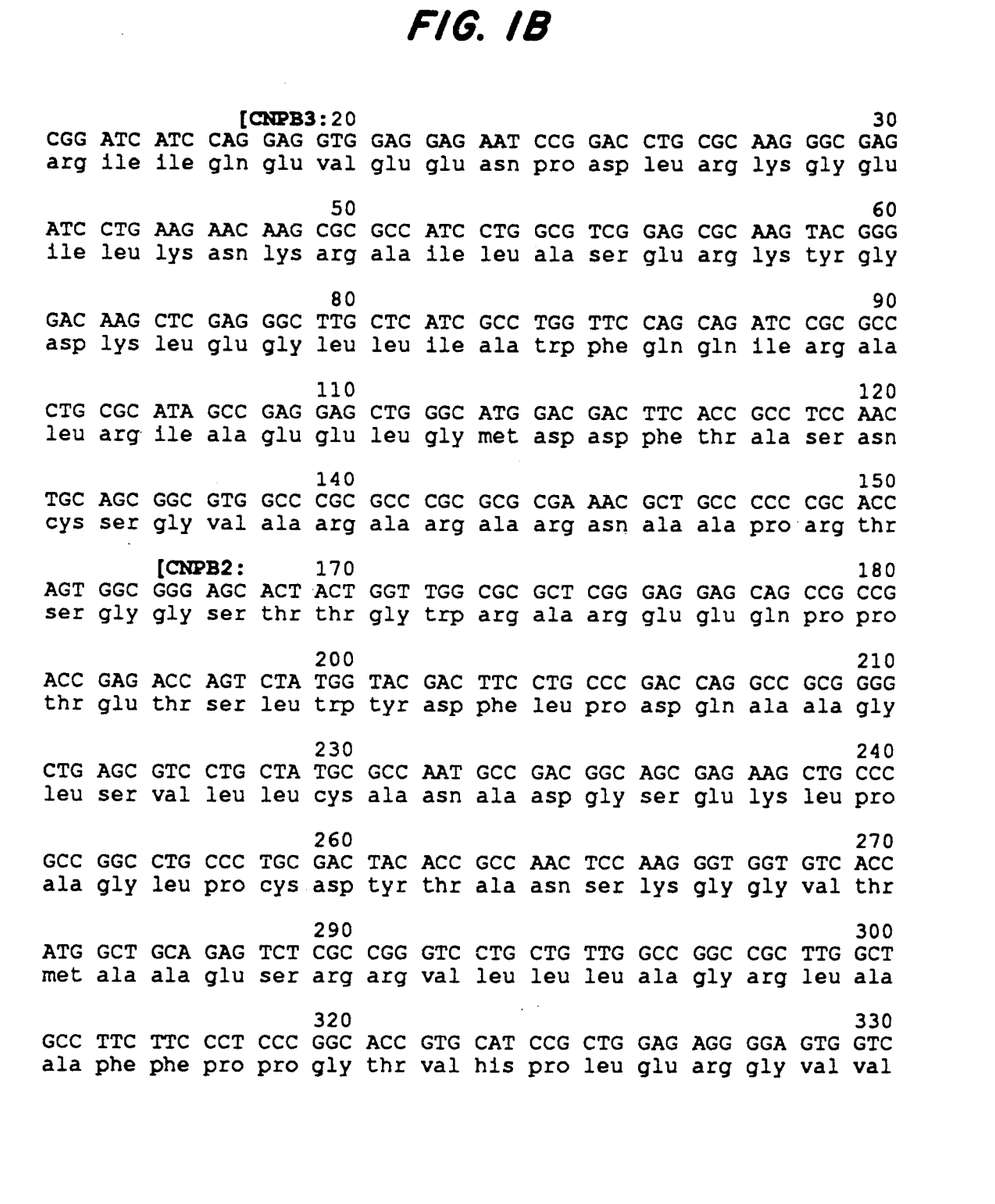
Figure 1C:
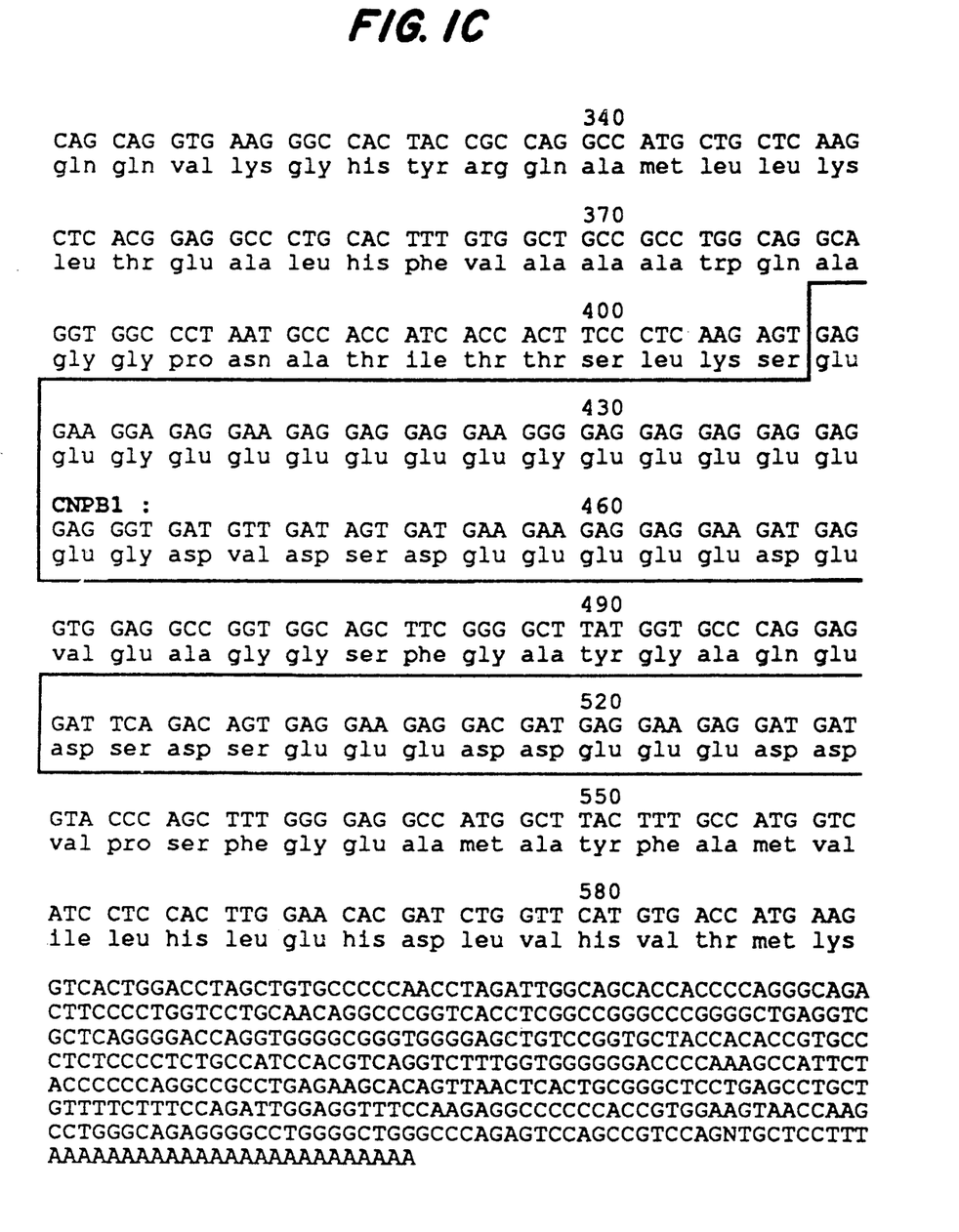
Figure 2:
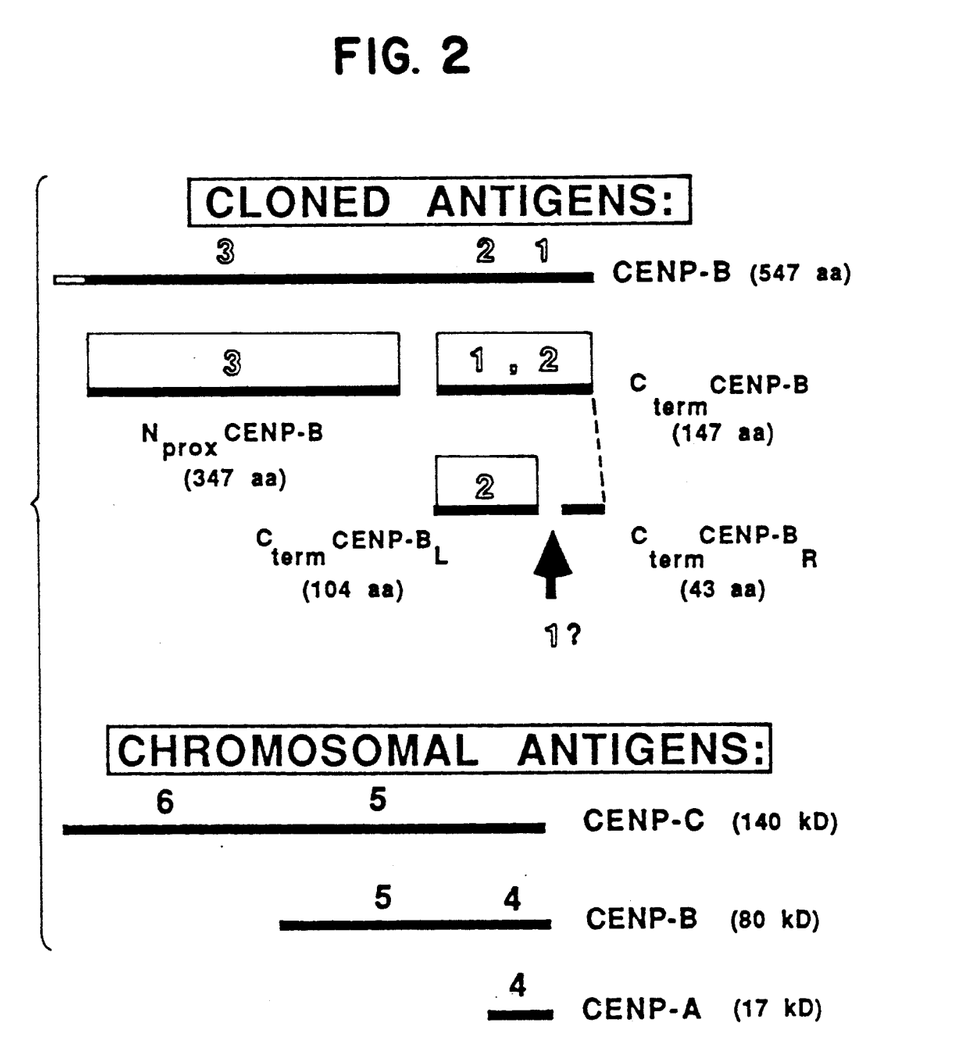
Figure 3:
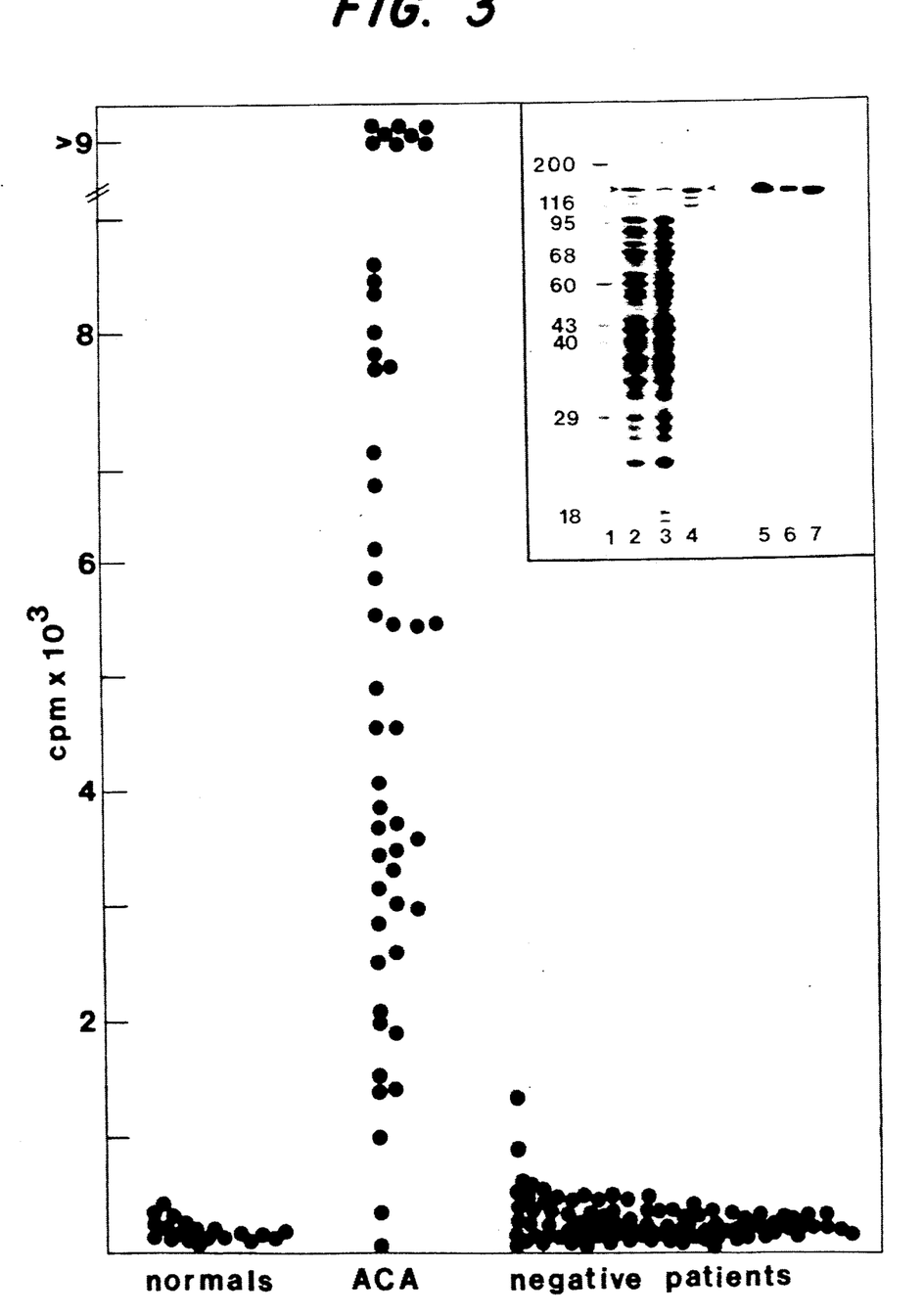

N$_{prox}$CENP-B is comprised of TrpE linked to 347 amino acid residues from teh amino-terminal region of CENP-B. The human portion of the protein encoded by this clone is separated in the CENP-B sequence by 98 amino acid residues from that encoded by C$_{term}$CENP-B (FIG. 2).

B. Localization of Centromere Epitope 1 (CE$_1$), a Major Autoepitope in the Carboxyl-Terminal Region of CENP-B To identify the epitope(s) in CENP-B that are targets for autoantibodies, the interactions of a panel of 37 ACA+ patient sera and 3 ACA− control sera with the cloned CENP-B polypeptide were examined. All patient sera were previously characterized by indirect immunofluorescence and immunoblotting against the proteins of isolated mitotic chromosomes (Earnshaw, et al, *Journal of Clinical Investigation*, 77: 426, 1986). Remarkably, all 37 ACA+ sera bound significantly to C$_{term}$CENP-B. Strong binding was evident for 86% (32 sera) and weaker binding characterized the remaining 14% (5 sera). Control sera did not bind the cloned antigen.

As described above, the murine monoclonal antibody, m-ACA1 recognizes a site (CE$_1$) present in C$_{term}$-CENP-B. It has been further determined that the site recognized by m-ACA1 corresponds to a major autoepitope on CENP-B. Nitrocellulose blots containing C$_{term}$CENP-B were cut into 40 strips, each of which was incubated overnight with a 1:50 dilution of human serum. Each strip was then probed with m-ACA1, the binding of which was detected with $^{125}$I-labeled goat anti-mouse IgG. Pretreatment of the blot strips with any of the 37 ACA+ sera blocked the binding of m-ACA1 to some extent, with 19 sera showing at least 80% blocking. The ACA+ sera least effective at blocking the binding of m-ACA1 (sera 8, 20, and 33), were also three of the poorest at binding to $C_{term}$CENP-B, suggesting that the variability of blocking of m-ACA1 may be largely due to variations in the titer of the anti-$C_{term}$-CENP-B autoantibodies.

To summarize, $CE_1$ is located in the carboxyl-terminal region of CENP-B and corresponds to the site which binds both murine monoclonal antibody m-ACA1 and autoantibody. Because disruption of $C_{term}$-CENP-B at a site 42 amino acids from the carboxyl terminus destroys the epitope recognized by m-ACA1, (FIG. 2) $CE_1$ spans this region of the protein, although loss of antigenicity might also result from a protein folding defect. Because of the close correspondence between the levels of binding observed with $C_{term}$-CENP-B[beta-gal] by RIA and with $C_{term}$CENP-B[trpE] by immunoblotting (FIG. 4B), it is apparent that $CE_1$ is the principal determinant being recognized in the RIA. $CE_1$ is recognized by virtually all ACA+ patient sera previously identified by indirect immunofluorescence.

C. $CE_2$, a Second Autoepitope in the Carboxyl-Terminal Region of CENP-B.

A minority of the panel of patient sera recognizes at least one other epitope ($CE_2$) in $C_{term}$CENP-B which was identified by immunoblotting of bacterial lysates expressing $C_{term}$CENP-$B_L$. Sera 6 and 9 recognized this hybrid protein (and a proteolytic fragment) strongly, whereas weaker binding was exhibited by sera 3, 13, 19, 24, 32, and 38 (making 22% in all).

The location of $CE_2$ was defined by a second murine monoclonal antibody, m-ACA2, previously shown to bind to $C_{term}$CENP-$B_L$. Three patient sera showed significant blocking of the binding of m-ACA2. The other five sera that bound $C_{term}$CENP-$B_L$ in immunoblots failed to block the binding of m-ACA2 to a significant degree, perhaps due to low titers of anti-$CE_2$ antibodies.

Even though all ACA+ sera bound to $C_{term}$CENP-B, only a handful (22%) recognized $C_{term}$CENP-$B_L$ and none recognized $C_{term}$CENP-$B_R$. Thus, all ACA+ sera tested recognized only one epitope in $C_{term}$CENP-B.

The data shows $CE_2$ is located within a 104 amino acid stretch starting 43 amino acids upstream from the carboxyl terminus of CENP-B. This epitope is recognized by only about 20% of the patient sera tested and, even in the sera that interact most significantly with it, anti-$CE_2$ comprises only a small fraction of the antibodies that recognize $C_{term}$CENP-B.

D. $CE_3$, an Epitope Present on N-Proximal CENP-B

To determine whether additional autoantibody binding sites occur outside the carboxyl-terminal region of CENP-B, the binding of the panel of 40 sera to $N_{prox}$-CENP-B in immunoblots was examined. Ninety percent (33) of the ACA+ sera showed significant binding, although intensity was much more variable than that observed with $C_{term}$CENP-B. Thus, a third autoepitope(s), $CE_3$, is localized within the amino-terminal 60% of CENP-B. This epitope is strongly recognized by a majority of ACA+ sera, but lower titers of anti-$CE_3$ ACA are present in most (or all) of the remaining ACA+ sera. Overall, about 90% of the ACA+ sera exhibit detectable binding to $CE_3$. $CE_1$ and $CE_3$ are distinct structural determinants, since affinity-purified anti-$CE_1$ and anti-$CE_3$ do not cross react.

Three additional autoepitopes recognized by ACA were previously identified by analysis of the binding of various affinity-purified patient sera to chromosomal antigens in immunoblots (Earnshaw, et al., *Chromosoma*, 91:313, 1985). The first of these, $CE_4$, is present on CENPs A and B and is absent from CENP-C (defined by sera GS and SN). Over 97% (38/39) of a panel of 39 ACA+ patient sera had anti-CENP-A detectable by immunoblotting (Earnshaw, et al., *Journal of Clinical Investigation*, 77, 426, 1986). It is likely that all sera binding to CENP-A bind to $CE_4$, although the structure of this antigen may be more complex. Epitope $CE_5$, shared by CENPs B and C, was defined by antibodies from serum JR, affinity-purified from CENP-C, that were subsequently found to cross-react strongly with CENP-B (Earnshaw, et al., *Chromosoma*, 91:313, 1985). Finally, $CE_6$, found solely on CENP-C, was defined when antibodies were affinity purified from CENP-C (using serum GS) that showed no rebinding to CENP-B (Earnshaw, et al., ibid). The pattern of binding observed using antibodies affinity purified from $CE_1$, $CE_2$, $CE_3$, $CE_4$, $CE_5$, and $CE_6$ indicates that all of these determinants are structurally independent (Earnshaw, et al., ibid).

E. Titer of ACA

The titers of autoantibodies from one serum (KG) against chromosomal CENPs A, B, and C and against two regions of cloned CENP-B were measured. The titer of antibodies specific for each antigen was determined by probing parallel blot strips of chromosomal proteins with serial dilutions of the patient serum. Positive signals were obtained in overnight exposures for the following serum dilutions: CENP-A, 1:1,638,400; CENP-B, 1:3,276,800; and CENP-C, 1:12,800.

Thus, though the titers of antibodies against CENPs A and B were comparable, antibodies to CENP-C were less abundant (roughly by a factor of 200). Note, however, that the three chromosomal antigens may be present in differing amounts. When the serum was titered against cloned $C_{term}$CENP-B, a positive signal was obtained at an antibody dilution of 1:4,096,000. The titer of antibodies recognizing $N_{prox}$CENP-B was also high, with a positive signal being observed at an antibody dilution of 1:512,000. The extraordinary titers measured in these experiments are substantially greater than the 10- to 30-fold increase observed subsequent to a nonspecific polyclonal lymphocyte activation, suggesting that ACA do not arise as a result of generalized derepression of the immune system.

F. Development of a Solid-Phase Binding Assay to Detect ACA $C_{term}$CENP-B[beta-gal] was purified to about 40% homogeneity as described infra (Example 7, B). Immunoblotting experiments confirmed that the soluble $C_{term}$CENP-B[beta-gal] retains reactivity with the autoantibodies (FIG. 2 inset, line 7).

A solid-phase RIA to screen was used with 48 ACA+ patient sera to determine binding to $C_{term}$-CENP-B[beta-gal]. Also tested were twenty sera from normal individuals and 92 ACA− patient sera. The latter included patients with Raynauds phenomenon and scleroderma (with or without full or partial CREST) as well as randomly chosen sera from individuals with systemic lupus erythematosus and Sjogren syndrome. Virtually every ACA+ patient serum bound to this portion of CENP-B (FIG. 2), except for two sera. These two sera were both characterized by the presence of substantial levels of anti-$C_{term}$CENP-B antibodies of the IgG3 subtype, which is not recognized by the detectably labeled protein A used in the assay. The average values for the three serum classes shown were: normal control sera, 195±100 cpm; ACA− patient sera, 284±187 cpm; and ACA+ patient sera, 6013±4809 cpm (a 22-fold stimulation for ACA+ sera over ACA− control sera).

Figure 4A:
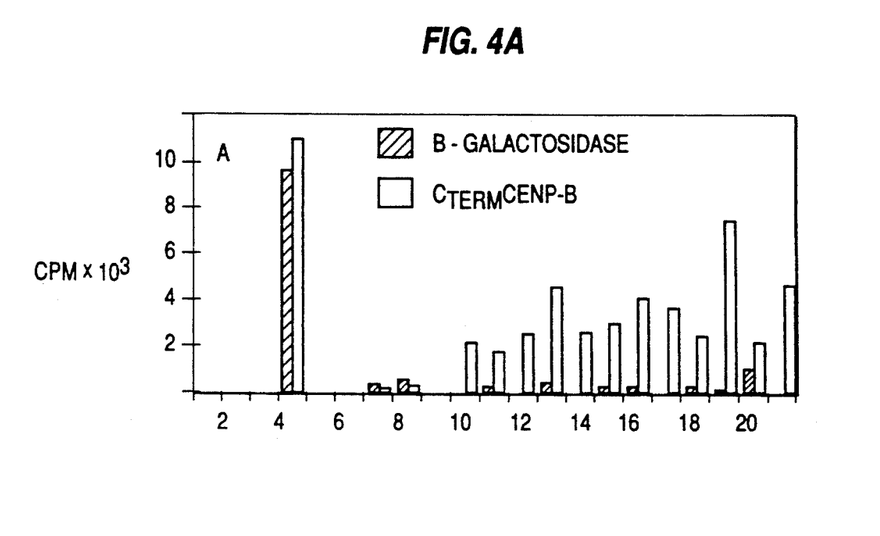
FIG. 4A: Test for the binding of a random panel of control and patient sera to B-galactosidase and $C_{term}$ CENP-B[beta-gal] by RIA. The sera used were normal controls (1-3), serum from a rabbit immunized with $C_{term}$ CENP-B[beta-gal] which contains both anti-CENP-B and anti-beta-galactosidase (4), ACA− patient control sera (5-9), and ACA+ patient sera (10-21).

In a control experiment, the binding of a number of randomly chosen ACA+ and ACA− sera to $C_{term}$-CENP-B[beta-gal] and to beta-galactosidase was examined (FIG. 4A). The latter comprises 87% of the mass of $C_{term}$CENP-B[beta-gal]. The rabbit antiserum elicted by injection with $C_{term}$CENP-B[beta-gal], described above, was included as a positive control. This serum bound to both substrates in this assay (FIG. 4A, lane 4). However, none of the patient or control sera exhibited significant binding to beta-galactosidase.

Figure 4B:
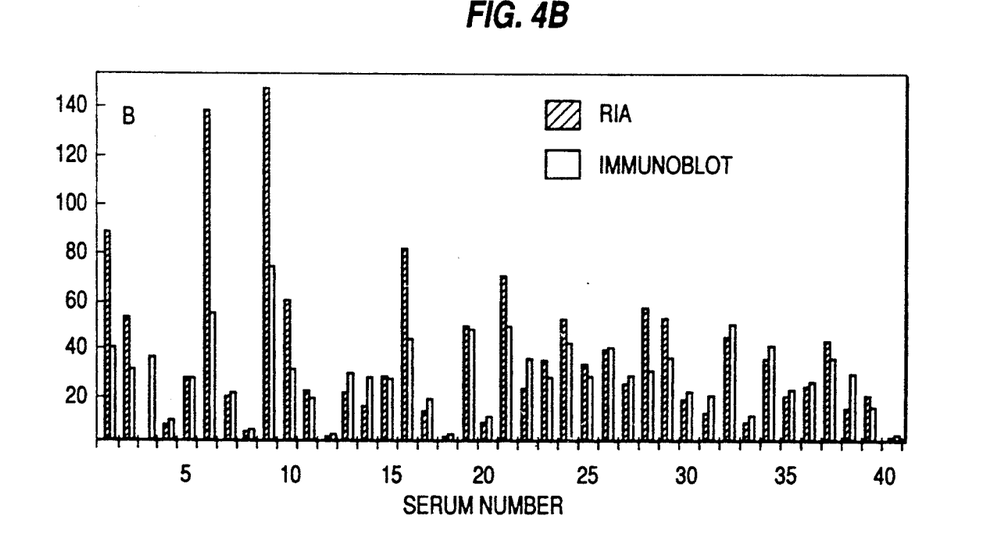

A quantitative immunoblotting assay also confirmed that the binding observed in the RIA was specific for the human portion of $C_{term}$CENP-B[beta-gal]. Bacterial lysates containing $C_{term}$CENP-B, fused to TrpE and therefore containing no bacterial sequences in common with $C_{term}$CENP-B[beta-gal], were subjected to NaDodSO$_4$/PAGE and immunoblotting. The region of the nitrocellulose containing the fusion protein with its bound autoantibody and $^{125}$I-labeled protein A was excised and counted in a gamma counter. The results for the panel of 40 sera are shown in FIG. 4B along with the values obtained for these same sera by RIA. The striking correlation exhibited by the two data sets confirms that the RIA detects the binding of autoimmune sera to the human portion of CENP-B.

EXAMPLE 7

Detection of Antibodies to CENP-B in Clinical Specimens

A. Patients

Immunoblotting, immunofluorescence, and ELISA assays were carried out on 347 patients and 34 normal controls (31 females; mean age 42.1, range 19–65 years). Patients were evaluated at the time of study when blood was obtained. The diagnoses of the patients is shown in Table II.

B. Preparation of Fusion Protein

An overnight culture of lysogen lambda-CENP-B1 was diluted 1:100 into 1 liter of L-broth (Maniatis, et al., ibid) at 30° C. and grown with shaking to O.D.$_{550}$=0.8. Phage production was induced at 42° C. for 15 min. IPTG (isopropyl beta-D-thiogalactopyranoside, Sigma, St. Louis, Mo.) was added to 5 mM, and the culture incubated at 37° C. for 4 hours. The bacteria were then centrifuged at 4,000× g for 10 minutes at 4° C. and the supernatant discarded. The pellet was resuspended in 10 ml of TEN buffer (10 mM Tris pH 7.7, 50 mM NaCl, 2 mM EDTA) and frozen in N$_2$ (Earnshaw, et al., *Arthritis and Rheumatism*, 30:1416, 1987). One tube (equivalent to ⅓ liter of culture) was thawed and TEN buffer added to 10 ml. All subsequent solutions contained a mixture of the following protease inhibitors: phenylmethylsulfonyl fluoride (0.1 mM), TRasylol (10 Kallikrein units/ml; Mobay Chemical, Pittsburgh, Pa), chymostatin, leupeptin, antipain and pepstatin (all used at 1 ug/ml; Sigma). Lysozyme (Sigma) was added to 1.5 mg/ml and EDTA to 5 mM.

This solution was sonicated (Branson sonifier with microtip) 30 seconds each at settings 3,4, and 5, and then incubated 10 minutes at 4 C. on a rotating mixer. Next, Triton X-100 (to 0.2%), several crystals of DNase 1 (Worthington, Freehold, N.J.), and MgCl$_2$ (to 10 mM) were added. This solution was mixed 10 minutes at 4° C. Unlysed cells and cell debris were removed by centrifugation at 4,000× g for 10 minutes and the supernatant transferred to a 50 ml plastic tube (Sorvall, Wilmington, Del.). To this was added 4 ml of 10% Triton X-100, 4 ml of 10× TEN buffer, and H$_2$O to 40 ml (step A) and the solution was sonicated at setting 4 (step B). The solution was then centrifuged at 12,000×g for 15 minutes at 4° C. and the supernatant discarded (step C). Steps A and B were repeated. The solution was centrifuged at 4,000 rpm for 10 minutes the pellet discarded, and the supernatant centrifuged as in step C. The resulting supernatant was discarded, and steps A through C were repeated.

To the final pellet were added 2 ml of 7.2M urea in TEN buffer. The solution was heated to 75° C. for 10 minutes, centrifuged 30 minutes at 15,600×g at 4° C., and the supernatant dialyzed overnight against TEN buffer, at 4° C. Using this isolation procedure, the recovery of $C_{term}$CENP-B [beta-gal] was calculated to be 1.07 mg/l of bacterial culture.

C. Immunofluorescence Tests for Anti-Centomere Antibody

Sera (diluted 1:40) were tested using HEp-2 cells and fluorescein-labeled rabbit anti-human Ig (Wampole Laboratories, Cranbury, N.J.) and further tested in the same dilution using fluorescein-labeled goat anti-human IgG (gamma chain specific; Kallestad Laboratories, Inc., Austin, Tex.) (Earnshaw, et al., ibid). In some instances, dilutions of serum at 1:10 and 1:20 were also tested.

None of the 34 normal controls had ACA. Eighty-patients had ACA at serum dilutions of 1:40 or greater. Titers ranged from 1:40 to 1:81,920. The diseases or syndromes of the ACA (+) patients are shown in Table II.

D. Immunoblotting

Immunoblotting was performed (Earnshaw, et al., ibid) using purified chromosomes and sera diluted 1:200. Using this technique anti-CENP-B was found in 82 of the 83 ACA (+) patients. The negative patient had a 1:1280 titer of ACA by immunofluorescence. When immunoblotting was repeated using goat anti-human IgG (Cooper Biomedical, Freehold, N.J.) prior to adding I$^{125}$ labelled Staph A, anti-CENP-B was detected in this specimen.

E. ELISA for $C_{term}$CENP-B Binding Antibodies

An optimal concentration of fusion protein (13.8 ug/ml) diluted in coating buffer (carbonate buffer, pH 9.6:1.59 gm Na$_2$CO$_3$, 2.93 gm NaHCO$_3$ made up to 1 liter with distilled water) was incubated on microtiter plates (Immulon II, Dynatech, Alexandria, Va.) and placed at 4° C. overnight. The antigen solution was then removed by aspiration and the plates washed three times with phosphate buffered saline (PBS)-Tween 20 (PBS, pH 7.4:80 g of NaCl, 2 g of NaPO$_4$, and 29 gm of Na$_2$HPO$_4$; with 0.5 ml Tween). Remaining free binding sites were blocked by adding 200 ul of 100 ug/ml bovine serum albumin (BSA) diluted in PBS and incubating the plates for 1 hour at 37° C.

Plates were aspirated and washed three times in PBS-Tween 20. 100 ul of test serum diluted 1:1500 was added per well. Plates were incubated at 37° C. for 1 hour, aspirated, and washed 3 times with PBS-Tween 20. 100 ul of peroxidase conjugated goat anti-human IgG (Tago, Inc., Burlingame, Calif.) diluted 1:1000 was added to each well and plates were incubated for 1 hour at 37° C. Next, the plates were aspirated and washed 3 times with PBS-Tween 20, before addition of 100 ul of substrate (150 ul of 2,2'-azino-di-3-ethyl-benzthiazaline sulfonic acid diammonium salt (Sigma) 10 ml citrate buffer (pH 4.0), 40 ul 3% H₂O₂). Plates were read using an ELISA reader (Dynatech) at 410-415 mu. All sera were tested in triplicate and the results were averaged. For each plate, the same positive serum was run in triplicate as positive control. For each plate, the O.D. of this high positive serum was considered to be 100% and the percent positive of the average O.D. for each test serum was calculated.

The results of the ELISA assay are shown in Table II. The ELISA (serum diluted 1:1500) was more sensitive than either immunofluorescence (serum diluted 1:40) or immunoblotting (serum diluted 1:200). The mean % positive for the 34 normal controls was 2.61%±1.23%. Therefore a percent of greater than 2 S.D. above the mean (5.07%) was considered a positive test. One (3%) of the 34 normals had a very weakly positive test of 5.10%. All of the 83 patients whose sera were positive by immunofluorescence were positive by ELISA. Of the 298 sera negative by immunofluorescence (both patient and control sera), 50 (17%) were positive by ELISA (Table II). These 50 sera were retested by immunofluorescence using serum diluted 1:10 and 1:20 and were negative. Of the 70 patients without Raynaud's syndrome or CREST (calcinosis, RS, esophageal dysmotility, sclerodactyly, telangiectasias), the ELISA was positive in 2 (3%).

TABLE II

Anticentromere Antibody Reactivity of Various Clinical Specimens As Determined By immunofluorescence and ELISA

| Disease/Syndrome | N | PERCENT POSITIVE | |
|---|---|---|---|
| | | immunofluorescence | ELISA |
| Raynaud's Disease | 104 | 18 | 34 |
| Scleroderma | 99 | 34 | 57 |
| CREST | 26 | 62 | 62 |
| Overlap Disease | 35 | 37 | 60 |
| SLE with RS | 13 | 7 | 15 |
| SLE without RS | 30 | 0 | 2 |
| Rheumatoid Arthritis | 33 | 0 | 0 |
| Eosinophilic fasciitis | 2 | 0 | 0 |
| Linear scleroderma | 1 | 0 | 0 |
| Morphea | 1 | 0 | 0 |
| Pulmonary fibrosis | 1 | 0 | 0 |
| Primary Sjogren's Syndrome | 2 | 0 | 0 |
| Total | 347 | 24 | 37 |
| Normal controls | 34 | 0 | 3 |

F. Blocking Studies

In order to study the specificity of the reaction with CENP-B, blocking experiments were carried out using fusion protein, Ro antigen, extractable nuclear antigen (ENA) rabbit thymus extract (Pel-Freeze, Rogers, AR), E. coli DNA, and Scl-70 calf thymus extract (Alpha Antigens, Columbia, Mo.). All proteins were used at concentrations of 6.9 mg/ml. Proteins were added to various dilutions (in PBS-Tween 20) of a serum positive for anti-fusion protein (1:200, 1:400, 1:800, 1:1600, 1:3200, 1:6400, 1:12800), and to the buffer alone. The mixture was incubated at 37° C. for 1 hour and then at 4° C. overnight. The ELISA as described above was then carried out.

At a serum dilution of 1:200, there was a 84% reduction in O.D. after absorption with fusion protein, 0% reduction with DNA, 5% with Ro, 19% with Scl-70, and 30% with ENA. For the test serum diluted 1:400, there was a 92% reduction with fusion protein, 12% with DNA, 27% with Ro, 26% with Scl-70 and 55% with ENA. Similar percent reductions occurred at dilutions 1:800 and 1:1600 of positive serum and at 1:3200, all O.D. readings were below 0.1. A diluted positive serum was absorbed with serial dilutions of fusion protein and the ELISA was then performed. The percent inhibition for the highest concentration of fusion protein (35 ug/ml) was 90.3% and for the lowest concentration (0.54 ug/ml) was 66.8%. An ELISA for antibodies to galactosidase was uniformly negative for all sera.

The invention now being fully described, it will be apparent to one of ordinary skill in the art that many changes and modifications can be made thereto without departing from the spirit or scope of the invention.

We claim:

1. A cDNA sequence comprising a cDNA sequence encoding a CENP-B polypeptide consisting essentially of an epitope reactive with at least 90% of those samples having anticentromere autoantibodies, wherein said epitope is destroyed by disruption at a site 42 amino acids from the carboxy terminus of CENP-B.

2. The cDNA sequence of claim 1, wherein said cDNA sequence encodes $C_{term}$ CENP-B.

3. A host cell transformed or transfected with the cDNA sequence of claim 2.

4. A biologically functional plasmid or viral DNA vector including the cDNA sequence of claim 2.

5. A host cell stably transformed or transfected with a DNA vector according to claim 4.

6. A cDNA sequence comprising a cDNA sequence encoding a CENP-B polypeptide consisting essentially of an epitope that immunologically corresponds to the CENP-B epitope reactive with at least 90% of those samples having anticentromere autoantibodies which immunologically binds the monoclonal antibody produced by the hybridoma deposited under ATCC Accession No. HB 9667.

7. A method of detecting autoantibodies to human CENP-B polypeptide which comprises:
(a) contacting a sample which may contain autoantibodies with a polypeptide encoded by the cDNA sequence of claim 1 or claim 6;
(b) incubating the components of step (a) for a period of time and under conditions sufficient for said autoantibodies to bind to said polypeptide;
(c) separating from said sample said polypeptide and any autoantibodies bound thereto; and
(d) detecting the presence of said autoantibodies bound to said polypeptide.

8. The method of claim 7 wherein said detecting utilizes a detectably labeled protein capable of binding to said autoantibody.

9. The method of claim 8 wherein said binding protein is a detectably labeled second antibody.

10. The method of claim 8 wherein said detectable label is selected from the group consisting of a radioisotope, a fluorescent compound, a colloidal metal, a chemiluminescent compound, a bioluminescent compound and an enzyme.

* * * * *